United States Patent [19]

Negrin et al.

[11] Patent Number: 5,084,208
[45] Date of Patent: Jan. 28, 1992

[54] PREPARATION OF DISCRETE MICRODROPLETS OF A HIGH VISCOSITY OIL IN WATER

[75] Inventors: Max Negrin, Goshen, N.Y.; Gary Dandreaux, Bloomfield, N.J.; Stephen L. Kopolow, Plainsboro, N.J.; William J. Burlant, Wayne, N.J.

[73] Assignee: ISP Investments Inc., Wilmington, Del.

[21] Appl. No.: 637,838

[22] Filed: Jan. 7, 1991

[51] Int. Cl.$^5$ ............................................. B01J 13/00
[52] U.S. Cl. ................................... 252/312; 252/308; 526/260; 526/911; 424/401
[58] Field of Search ................. 264/4.1, 4.7; 252/308, 252/312; 526/260, 911; 524/801; 424/401

[56]  References Cited
U.S. PATENT DOCUMENTS

| | | | |
|---|---|---|---|
| 2,969,330 | 1/1961 | Brynko | 252/316 |
| 3,016,308 | 1/1962 | Macaulay | 117/36.7 |
| 3,516,941 | 6/1970 | Matsoil | 252/316 |
| 3,763,347 | 10/1973 | Whitaker | 219/275 |
| 4,251,386 | 2/1981 | Saeki et al. | 252/316 |
| 4,976,961 | 12/1990 | Norbury et al. | 424/401 |

*Primary Examiner*—Robert L. Stoll
*Assistant Examiner*—Nina Bhat
*Attorney, Agent, or Firm*—Walter Katz; Marilyn J. Maue; Joshua J. Ward

[57] ABSTRACT

What is provided herein is a method for preparing discrete microdroplets of a high viscosity oil in water stabilized by in situ polymerization of a water-soluble vinyl monomer. The method comprises dispersing the oil in water containing a surfactant, adding the water-soluble vinyl monomer, preferably vinylpyrrolidone, optionally with a comonomer, and polymerizing the monomer or comonomers in situ such that the oil is stabilized in the resulting polymer solution as discete microdroplets.

32 Claims, No Drawings

PREPARATION OF DISCRETE MICRODROPLETS OF A HIGH VISCOSITY OIL IN WATER

BACKGROUND OF THE INVENTION

1. Field of the Invention

This invention relates to a method for stabilization of oils in water, and more particularly, to a method for preparing stable, discrete microdroplets of a high viscosity oil in water stabilized by an in situ produced water-soluble polymer solution and a surfactant.

2. Description of the Prior Art

The unique properties of many oils make it desirable to include them in aqueous-based compositions. For example, cosmetically-active materials such as silicone oils, fluids and gums, mineral oils, and water-insoluble organic esters such as isopropropyl palmitate and isopropyl myristate, are particularly useful in cosmetic formulations for the skin and hair. In such compositions, their lubricity properties impart conditioning action for the user. However, such oils are immiscible with water which makes it very difficult to maintain a stable aqueous dispersion without rapid separation of the composition into oil and water phases. To solve the problem of providing effective dispersibility of such materials in water, it has been necessary to include a surfactant in aqueous cosmetic compositions containing cosmetically-active oils in order to maintain dispersed droplets of the oil in the aqueous solution. However, even with a surfactant present, the stability of the dispersion is often not completely satisfactory, particularly where high viscosity oils are used.

Another approach is to form macroscopic capsules of an oil by in situ aqueous polymerization of oil soluble monomers. For example, Brynko, in U.S. Pat. Nos. 2,969,330 and 2,969,331, described the preparation of pressure-rupturable capsules of a chlorinated diphenyl oil in water by dissolving styrene, an acrylate or vinyl acetate monomer in the oil, dispersing the monomer-containing oil in water with the aid of an emulsifier to form droplets, and polymerizing the monomer to form an encapsulating wall of solid polymer material around each droplet of oil.

Berg, in *J. Microencapsulation* (1989) 6, No. 3, 327–337, also described a process for the microencapsulation of emulsified oil droplets by in situ vinyl polymerization. However, the process was limited to the use of methyl methacrylate, an oil soluble monomer, to form a polymer shell around emulsified oil droplets of decane and hexadecane.

De Luca, in U.S. Pat. No. 4,741,872, described the preparation of biodegradable microspheres having a three-dimensional network in which biologically active macromolecular agents were physically entrapped therein. The method involved emulsifying a vinyl derivative of a biodegradable hydrophilic polymer, a water-soluble monovinyl monomer, and a biologically active macromolecular agent, in water, and copolymerizing the vinyl compounds.

However, these and other processes have not provided a method by which cosmetically active oils, such as silicone oils, can be prepared as a stable dispersion in an aqueous medium. Nor does the prior art suggest a procedure for allowing oils of high viscosity to maintain themselves effectively in stable condition in an aqueous cosmetic formulation.

Accordingly, it is an object of the present invention to provide a process for stabilizing oils in water, preferably in the form of microdroplets, maintained discretely and for an extended period of time in an aqueous medium.

Another object of this invention is to provide a method for preparing an aqueous composition which includes stable, discrete microdroplets of an oil, including an oil of high viscosity, dispersed therein.

Still another object of the present invention is to provide a method of preparing a composition in which microdroplets of oils of high viscosity are homogeneously distributed in the composition.

Yet another object is to provide such stable, dispersed microdroplets by in situ polymerization of a water-soluble vinyl monomer, such as vinylpyrrolidone, in the presence of dispersed droplets of a water-insoluble oil, such as silicone oil, including high viscosity oils, in water containing a surfactant.

Among the other objects of the invention is to provide a cosmetic formulation containing stable, discrete microdroplets of a cosmetically-active oil stabilized in an aqueous solution in situ polymerized vinylpyrrolidone.

These and other objects and features of the invention will be made apparent from the following description thereof.

ABBREVIATIONS AND DEFINITIONS

Oil - A compound which is a water-insoluble liquid at room temperature and has an oily consistency VP - Vinylpyrrolidone MAPTAC - Methacrylamidopropyltrimethylammonium chloride PVP - Polyvinylpyrrolidone DM - Polydimethylsiloxane, Dimethicone, 100 cs, Petrarch Chem. Co; 1000 cs, Dow Corning Corp.

TBP - Tert-butyl peroctoate, e.g. Trigonox® 21 (AKZO Chem. Co.)

Cosmetically-active oil - An oil which imparts a particularly desirable property, e.g. lubricity, to a cosmetic formulation Brookfield viscosity - Viscosity of Stabilized Oil in Water Product in cps, as measured using a RVT spindle #3@70 rpm

SUMMARY OF THE INVENTION

What is provided herein is a method for preparing stable, discrete microdroplets of an oil of high viscosity in water stabilized in a polymer solution of an in situ polymerized, water-soluble vinyl monomer. The method comprises dispersing the oil in water containing a surfactant to form microdroplets, adding a water-soluble vinyl monomer, such as vinylpyrrolidone, optionally with a comonomer, such as methacrylamidopropylammonium chloride, and polymerizing the monomer or comonomers in situ such that the oil droplets are stabilized in the resultant aqueous polymer solution.

In the preferred form of the invention, the oil is cosmetically-active, such as is characteristic of silicone oils, mineral oils and water-insoluble esters such as isopropyl myristate and isopropyl palmitate.

DETAILED DESCRIPTION OF THE INVENTION

The active material to be dispersed in an aqueous medium are oils which are water-insoluble liquids at room temperature, and preferably, are cosmetically-active, i.e. they impart a particularly desirable property to cosmetic formulations. Such cosmetically-active oils include silicone oils, mineral oils and water-insoluble esters such as isopropyl myristate and isopropyl palmitate.

Suitable silicone oils or fluids for use in the invention may be selected from non-volatile polyalkyl siloxanes, polyaryl siloxanes, polyalkylaryl siloxanes and polyether siloxane copolymers. Such silicone oils usually are present in the composition at a level of from about 1.0% to about 18%, preferably about 2.0% to about 8.0%. Mixtures of these compounds also may be used as long as the final mixture is non-volatile and the dispersed silicone particles are insoluble in the aqueous medium. As used herein, "insoluble" requires that the oil does not substantially dissolve in water and is essentially immiscible therewith.

Non-volatile polyalkylsiloxanes include, for example, polydimethylsiloxanes (Dimethicone) with viscosities ranging from about 5-600,000 centistokes (cs) at 25° C. These siloxanes are available, for example, from the General Electric Company as the VISCASIL series and from Dow Corning as the Dow Corning 200 products. Their viscosity can be measured by the glass capillary viscometer procedure set forth in Dow Corning Corporate Test Method CTM 0004 issued July 20, 1970. Preferably, the viscosity of these siloxanes selected have a viscosity of about 100 to about 300,000 cs.

Suitable non-volatile polyalkylarylsiloxanes include, for example, polymethylphenylsiloxanes having viscosities of about 15 to 65 cs at 25° C. These siloxanes are available for example, from the General Electric as SF 1075 methylphenyl fluid or from Dow Corning as 556 Cosmetic Grade Fluid. Additionally, poly(dimethylsiloxane) (diphenylsiloxane) copolymers having a viscosity in the range of about 10 to 100,000 cs at 25° C. are useful.

These and other suitable silicones are disclosed in U.S. Pat. Nos. 2,826,551, 3,964,500 and 4,364,837; and British Patent 849,433. The disclosures of these patents are incorporated by reference herein, as is the booklet "Silicone Compounds", which was distributed by Petrarch Systems Inc. in 1984, and which describes the preparation and properties of available silicones for use in this invention.

Other suitable oils for use herein include cosmetically-active materials such as light and heavy mineral oils, and water-insoluble organic esters such as isopropyl palmitate and isopropyl myristate.

In the practice of the present invention, the oil to be dispersed is first added to water containing a surfactant and then subjected to agitation to produce a fine dispersion of discrete oil microdroplets throughout the aqueous medium. The mixture is agitated sufficiently so that the dispersion is stable for a period of at least 5 to 10 minutes without separating into individual layers. Conventional laboratory and high speed agitators may be used for this purpose, as for example, conventional anchor or wide-span turbine agitators.

Suitable surfactants for use herein include nonionic, synthetic anionic, amphoteric and zwitterion surfactants, preferably present at a level of about 0.01 to 10% by weight of the polymerization mixture. A mixture of nonionic surfactants are preferred, which are available as Emulphogene BC-610 and BC-840 which have HLB values of about 11 and 14, respectively.

Thereafter, a water-soluble vinyl monomer, for example, a vinylpyrrolidone monomer such as vinylpyrrolidone itself or a derivative thereof such as an alkyl vinyl pyrrolidone, is added to the mixture, along with an appropriate free radical polymerization initiator. If desired, a comonomer is added for purposes of forming a copolymer. Suitable comonomers include dimethylaminopropyl methacrylate, dimethylaminoethyl methacrylate, methacrylamidopropyltrimethylammonium chloride, acrylamide and neutralized acrylic acid.

Suitable free radical polymerization initiators for polymerization of water-soluble vinyl monomers include such free radical catalysts as t-butylperoctoate, t-butylperoxy pivalate and the like. Oil-soluble catalysts are preferred.

Thereafter, the reaction mixture is maintained at a temperature in the range of about 55° to 85° C., preferably, about 75° to 85° C., and most preferably, about 78° to 82° C., for a period of time sufficient to effect the desired polymerization and form the aqueous polymer solution necessary to stabilize the discrete microdroplets of the oil.

As the polymerization proceeds, the dispersed oil droplets become white and appear to precipitate in the aqueous medium, however, without coalescing. Generally, the observance of this white or milky color in the aqueous medium is an indication of completion of the process, which usually takes about 2 to 20 hours, preferably about 4 to 10 hours, and most preferably, about 6 to 8 hours. After completion of polymerization, the residual vinyl monomer content generally is less than about 0.1%, as measured by the iodine titration method.

Suitably, the ratio of monomer to oil used in the polymerization should be in the range of about 95/5 to 5/95, respectively, on a weight basis, preferably at least about 50/50. Most preferred is a range of about 90/10 to 70/30. As used herein, a "stable composition or suspension" means that the discrete oil microdroplets remain suspended in the aqueous polymer solution for at least seven days at ambient temperature.

The viscosity of the stabilized oil in water product, for example, polyvinylpyrrolidone polymer which is, obtained by in situ polymerization of vinylpyrrolidone monomer, suitably is in the range of about 100 to 100,000 cps, preferably about 1,000 to 60,000 cps, and most preferably, about 3,000 to 25,000 cps.

The diameter of the oil microdroplets obtained are observed to be in the range of about 0.1 to 450 microns, and usually are about 1 to 100 microns.

The invention will now be described with references to the following more particular examples.

EXAMPLE 1

In Situ Polymerization of Vinylpyrrolidone in an Aqueous Dispersion of Polydimethylsiloxane having a Viscosity of 12,500 cs in Presence of a Surfactant A mixture of 15.3 g. of polydimethylsiloxane and 1.6 g. of Emulphogene BC 610 (Rhone-Poulenc Inc.), a nonionic surfactant, having an HLB value of 11, was formed with the aid of a homogeneizer. Then 2.4 g. of Emulphogene BC 840, another nonionic surfactant, having an HLB value of 14, was admixed with further stirring. Thereafter 50 g. of distilled, deionized water was slowly introduced into the mixture in increments of 10 ml. After each addition, the aqueous mixture was homogenized. A creamy, white emulsion was formed. Then an additional 550 g. of water was added slowly while stirring vigorously.

The resulting emulsion was transferred to a polymerization kettle equipped with a dropping funnel, water condenser, a N₂ inlet, an overhead stirring motor and a metal stirrer. The mixture was stirred at 200 rpm, purged with N₂ for 1 hour, 0.506 g. of Trigonox 21 was added, and the reaction mixture was heated to 82° C. After 20 minutes, a solution of 135 g. of freshly distilled vinylpyrrolidone and an additional amount of 0.301 g. of Trigonox 21 was added through the dropping funnel over 30 minutes. After the addition was completed, an exotherm was observed which raised the temperature of the reactants to 87° C. Polymerization was carried out at 82° C. and continued until the unreacted vinylpyrrolidone monomer content dropped to 0.53%. The resulting product was a white, homogeneous, aqueous polymer composition containing dispersed microspheres of PVP in which the siloxane was entrapped. The microspheres remained uniform upon standing for an extended period of time and did not coalesce.

EXAMPLES 2-6

The procedure of Example 1 was followed using polydimethylsiloxanes having a kinematic viscosity in the range of 100 to 100,000 cs, at a pH in the range of about 4.0 to 7.5. White, liquid, homogeneous products were obtained which remained uniform upon standing.

TABLE 1

| Ex. No. | Monomer | Amt (g) | Silicone Oil | Amt (g) | Viscosity (cs) | MW |
|---|---|---|---|---|---|---|
| 1-140 | VP | 135 | DM | 15.3 | 12,500 | 67,700 |
| 2-142 | VP | 135 | DM | 16.0 | 100,000 | 139,000 |
| 3-147 | VP | 135 | DM | 15.0 | 12,500 | 67,700 |
| 4-151 | VP | 135 | DM | 15.0 | 100,000 | 139,000 |
| 5-143 | VP | 135 | DM | 15.0 | 100 | 5,970 |
| 6-144 | VP | 135 | DM | 15.0 | 1,000 | 28,000 |

TABLE 2

| Ex. No. | Surfactant | Amt (g) | HLB | Medium | Amt (g) | pH | Initiator | Amt (g) | Agitation (rpm) |
|---|---|---|---|---|---|---|---|---|---|
| 1-140 | EPG BC-610 | 1.6 | 11.4 | Water | 600 | 4.0 | TBP | 0.81 | 200 |
|  | EPG BC-840 | 2.1 | 15.4 |  |  |  |  |  |  |
| 2-142 | BC 610/840 | 2.5/9.9 | — | Water | 600 | 4.0 | TBP | 0.76 | 200 |
| 3-147 | BC 610/840 | 1.7/2.5 | — | Water | 600 | 7.5 | TBP | 0.76 | 200 |
| 4-151 | BC 610/840 | 2.5/9.10 | — | Water | 600 | 7.5 | TBP | 0.78 | 200 |
| 5-143 | BC 610/840 | 1.7/2.5 | — | Water | 600 | 7.5 | TBP | 0.77 | 200 |
| 6-144 | BC 610/840 | 1.7/2.5 | — | Water | 600 | 7.5 | TBP | 0.77 | 200 |

TABLE 3

| Ex. No. | % Solids | Brookfield Viscosity (cps) |
|---|---|---|
| 1-140 | 19.2 | 220 |
| 2-142 | 19.7 | 216 |
| 3-147 | 20.0 | 8,170 |
| 4-151 | 20.0 | 7,300 |
| 5-143 | 20.0 | >8,000 |
| 6-144 | 20.0 | 10,160 |

The composition of the invention find particular use in the cosmetic industry, including cosmetic formulations for personal care products such as hair and skin care. In these products, the lubricity imparted by the oil and the film-forming characteristics of polyvinylpyrrolidone are advantageous properties for the user.

While the invention has been described with particular reference to certain embodiments thereof, it will be understood that changes and modifications may be made which are within the skill of the art. Accordingly, it is intended to be bound only by the following claims, in which:

What is claimed is:

1. A method for stabilizing an oil in water which comprises dispersing the oil in water and a surfactant as microdroplets, adding a water-soluble vinyl monomer and a free radical polymerization initiator thereto, and in situ polymerizing said monomer whereby the oil microdroplets are stabilized in the resulting polymer solution.

2. A method according to claim 1 wherein said water-soluble vinyl monomer is vinylpyrrolidone.

3. A method according to claim 1 wherein a water-soluble comonomer is included in the polymerization mixture.

4. A method according to claim 3 wherein said comonomer is methacrylamidopropyltrimethylammonium chloride.

5. A method according to claim 1 wherein said stabilized microdroplets are homogeneously distributed throughout the polymer solution.

6. A method according to claim 1 wherein said oil is a cosmetically-active material.

7. A method according to claim 1 wherein said oil is a silicone having a viscosity between about 5 to 600,000 cs.

8. A method according to claim 7 wherein said silicone has a viscosity between about 100 and 300,000 cs.

9. A method according to claim 2 wherein the weight ratio of the vinylpyrrolidone monomer to oil in the polymerization mixture is about 95:5 to 5:95, respectively, on a weight basis.

10. A method according to claim 9 wherein said weight ratio is about 90:10 to about 50:50.

11. A method according to claim 1 wherein said in situ polymerization is carried out at a temperature of about 55° to about 85° C.

12. A method according to claim 2 wherein the Brookfield viscosity of the stabilized oil in water product obtained upon in situ polymerization is about 100 to 100,000 cps.

13. A method according to claim 1 wherein the particle sizes of the stabilized, discrete microdroplets of oil are in the range of about 0.1 to 450 microns in diameter.

14. A method according to claim 1 wherein the free radical polymerization initiator is oil soluble.

15. A method according to claim 14 wherein said initiator is t-butylperoctoate.

16. A method according to claim 6 wherein said oil is a mineral oil or a water-insoluble organic ester.

17. A method according to claim 16 wherein said ester is selected from isopropylmyristate and isopropylpalmitate.

18. A method according to claim 10 wherein said ratio is about 90:10 to about 70:30.

19. A method according to claim 13 wherein said diameter of said particles is about 1 to 100 microns, and said Brookfield viscosity of the stabilized oil in water product is about 1,000 to 60,000 cps.

20. A method according to claim 19 wherein said Brookfield viscosity is about 3,000 to 25,000 cps.

21. A method according to claim 1 wherein in situ polymerization is carried out under vigorous agitation of the polymerization mixture until a milky suspension is obtained and the residual monomer content of the product is less than about 0.5%.

22. A method according to claim 5 wherein said silicone is a non-volatile polyalkyl siloxane, a polyaryl siloxane, a polyalkylaryl siloxane or a polyether siloxane.

23. A method according to claim 22 wherein said silicone oil is a polydimethyl siloxane.

24. A method according to claim 1 wherein the surfactant is a nonionic surfactant.

25. A method according to claim 1 wherein said surfactant is a mixture of nonionic surfactants having HLB values of about 11 and 14.

26. A method according to claim 2 wherein said polymerization is carried out at a pH of about 4 to 7.5.

27. A method according to claim 26 wherein said pH is at least 7.5.

28. A method according to claim 1 wherein said surfactant is present in an amount of about 0.01 to 10% by weight of the polymerization mixture.

29. The product of the method of claim 1.

30. The product of the method of claim 2.

31. The product of the method of claim 7.

32. The product of the method of claim 7 wherein said silicone is a non-volatile polyalkyl siloxane, a polyaryl siloxane, a polyalkylaryl siloxane or a polyether siloxane.

* * * * *